United States Patent [19]

Kosaka et al.

[11] Patent Number: 5,426,499
[45] Date of Patent: Jun. 20, 1995

[54] PARTICLE ANALYZING APPARATUS AND METHOD WHEREIN A ONE DIMENSION IMAGE SENSOR OPTICALLY TRACKS A PARTICLE

[75] Inventors: Tokihiro Kosaka, Kakogawa; Yasunori Maekawa, Miki, both of Japan

[73] Assignee: Toa Medical Electronics Co., Ltd., Hyogo, Japan

[21] Appl. No.: 138,013

[22] Filed: Oct. 19, 1993

[30] Foreign Application Priority Data

Oct. 21, 1992 [JP] Japan ................................. 4-307505
Dec. 3, 1992 [JP] Japan ................................. 4-350481

[51] Int. Cl.⁶ ...................... G01N 33/49; G01N 21/64
[52] U.S. Cl. ................................. 356/39; 250/461.2; 356/73
[58] Field of Search ..................... 356/23, 24, 39, 72, 356/73; 250/461.2

[56] References Cited

U.S. PATENT DOCUMENTS 4,338,024  7/1982  Bolz et al. ........................... 356/23

FOREIGN PATENT DOCUMENTS 2-105041  4/1990  Japan .
3-329835  2/1991  Japan .
3-150444  6/1991  Japan .

*Primary Examiner*—Vincent P. McGraw

[57] ABSTRACT

A particle image analyzing apparatus including, a flow cell for enclosing a solution containing a particle to be analyzed in a sheathed flow to form the solution into a sample solution flow, an irradiation optical system for emitting light to irradiate the sample solution flow, a one dimension image sensor for receiving the light transmitted through the particle to scan the particle and output an image signal, an optical deflection device, including a variable deflection angle, for deflecting the transmitted light introduced to the image sensor, a controller for controlling the deflection angle of the optical deflection device such that the image sensor optically tracks the particle, and a signal processor for processing the output image signal of the image sensor to analyze the particle.

22 Claims, 10 Drawing Sheets

PARTICLE ANALYZING APPARATUS AND METHOD WHEREIN A ONE DIMENSION IMAGE SENSOR OPTICALLY TRACKS A PARTICLE

BACKGROUND

1. Field of the Invention

The present invention relates to an apparatus for forming a sample solution containing particles (hemocytes or cells), such as blood or urine, into a sheathed flow, irradiating the sample solution flow with light, and detecting light from the particles to analyze the particle components. More particularly the invention relates to a particle analyzing apparatus such as a flow cytometer in which a one dimension sensor (for example a line sensor) detecting system is utilized to detect particles flowing through a flow cell and to measure light absorbencies of the particles.

2. Description of the Related Art

Apparatus for analyzing properties of particles traveling in a solution by irradiating them with light are conventionally known, for example a flow cytometer, a cell sorter, or an imaging flow cytometer.

U.S. Pat. No. 4,338,024 describes an image analyzing apparatus for forming a flat sample solution (flat sheathed flow) in a flow cell, and irradiating the solution with strobe light to obtain a still picture of particle components.

Japanese Patent Laid-Open (Kokai) No. HEI 2 (1990)-105041 discloses a particle image analyzing apparatus that uses optical deflection elements to obtain data on each portion of a particle by scanning an optical beam in a direction running crosswise relative to the direction in which particles travel, and detecting light passing through the inside of particles with an array type light detector.

Japanese Patent Laid-Open (Kokai) No. HEI 3 (1991)-29835 discloses an apparatus comprising parallel flat glass plates mounted on an optical axis for rotating the glass plates to shift light and adjust the optical axis. The object of rotating the glass plate is to adjust the optical axis in order to obtain the most favorable optical alignment.

Japanese Patent Laid-Open (Kokai) No. HEI 3 (1991)-150444 discloses a particle analyzing apparatus comprising an acousto-optic element that scans a particle with a laser beam in a horizontal direction (which runs at right angle to the direction of the flow of particles) and an acousto-optic element which moves the laser beam in a vertical direction thereby making it possible to scan one particle a plurality of times. The apparatus also adjusts the scanning rate in the flow direction such that it is slower than the flow rate. Both Japanese Laid-Open Patent No. HEI 2(1990)-105041 and Japanese Laid-Open Patent No. HEI 3(1991)-150444 describe a particle image analyzing apparatus in which light is scanned at a high rate in the horizontal direction, which may result in unstable operation. Further, Japanese Laid-Open No. HEI 3(1991)-150444 discloses that particles are scanned a plurality of times by allowing light to track the travel of particles. As a result, a center of one particle is scanned several times, but other portions of the particle are not scanned at all. Still further, the scan rate in the flow direction is reduced to improve the probability that the laser beam is fired onto the center of the particle.

Conventional flow cytometers are not capable of obtaining morphological data of each particle (such as area and circumferential length thereof). In addition, a very expensive video camera and image processing apparatus with high performance are required for obtaining real time characteristics of each particle by forming a sample into a flat flow, irradiating the sample with strobe light and processing an image of the particle captured with a video camera.

Therefore, the present inventors have invented a particle image analyzing apparatus which determines in real time, morphological data of each particle and a quantity of absorbed light by adding to a conventional flow cytometer, a detecting system based on a one dimension image sensor (line sensor) and a signal processing system, scanning an image of the particles that flow through a flat sheathed flow cell and processing detected signals obtained in the process (U.S. Ser. Nos. 07/937,340 and 08/070,687).

SUMMARY OF THE INVENTION

The present invention provides a particle image analyzing apparatus comprising: a flow cell for enclosing a solution containing particles to be analyzed in a sheathed flow to form the solution into a sample solution flow; an irradiation optical system for emitting light to irradiate the sample solution flow; a one dimension image sensor for receiving the light transmitted through the particle to scan the particle and output an image signal; optical deflection means, including a variable deflection angle, for deflecting the transmitted light introduced to the image sensor; control means for controlling the deflection angle of the optical deflection means such that the image sensor optically tracks the particle; and signal processing means for processing the output image signal of the image sensor to analyze the particle.

DESCRIPTION OF THE PREFERRED EMBODIMENTS

Figure 1A:
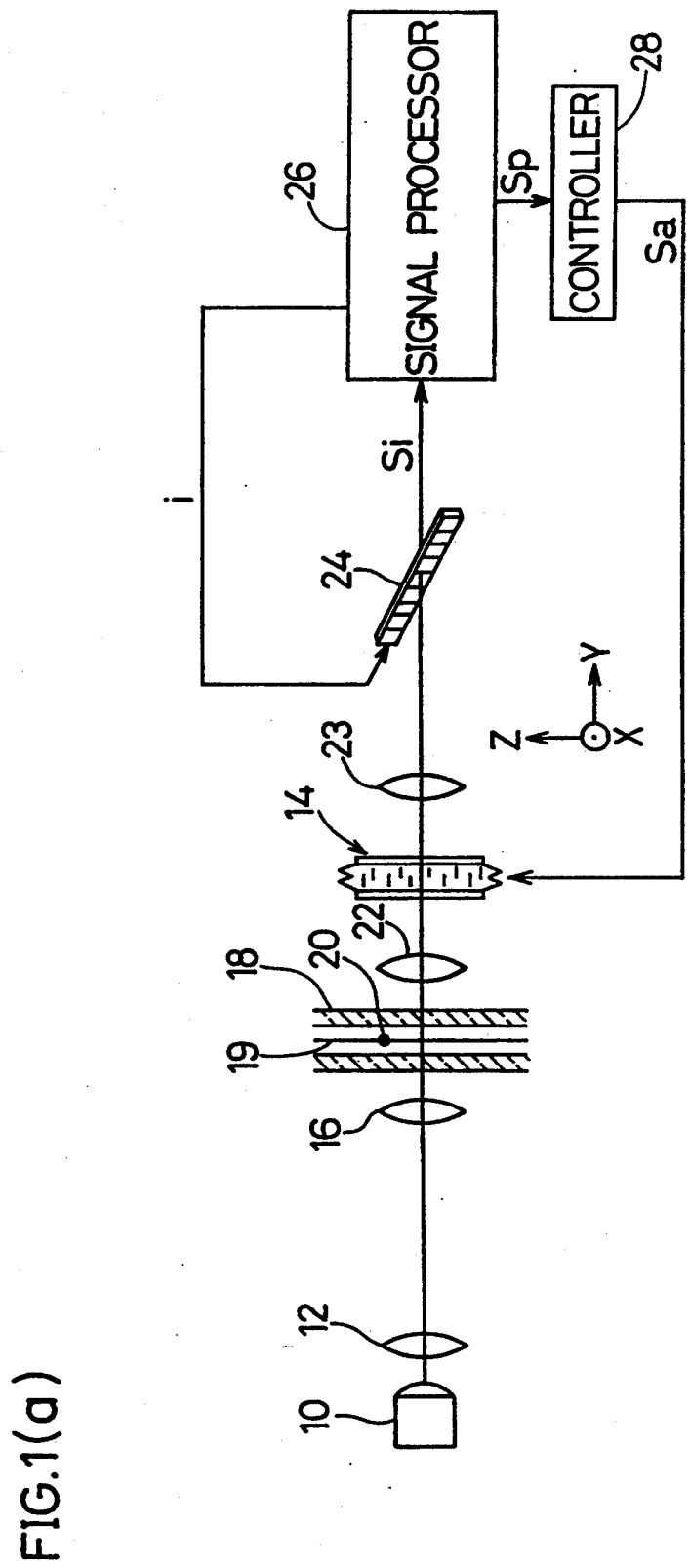
FIG. 1(a) is a side view illustrating a first embodiment of a particle image analyzing apparatus including an angle variable prism.

The particles to be analyzed according to the present invention include a hemocyte and a cell of a living body such as a human being or an animal. It may also include particles treated with fluorescent dyes or substances.

In addition, a sheathed flow is a flow that allows the passage of a sample solution containing particles to be detected by enclosing the sample solution with a layer stream of a sheathed solution and arranging a row of particles in the center of the sheathed solution with good accuracy.

The sample solution flow may be rectangular, ellipsoidal or circular in cross section. Preferably the sample solution that flows in the sheathed flow has an approximately rectangular or ellipsoidal cross section, and the thickness of the flow is approximately the same as the particle diameter. Preferably the width of the flow is several times larger than the particle diameter.

A conventional type flow cell can be used.

The irradiation optical system according to the present invention may comprise optical elements such as a light source, a lens, a prism, and a reflection mirror. Examples of the light source are a white light source and a laser beam source.

Preferably, the irradiation optical system is arranged so that the system irradiates a wider side of the flow of the sample solution, when the flow is rectangular or ellipsoidal.

Preferably, as the one dimension image sensor (line sensor), a sensor such as a CCD line sensor is used in which a plurality of light detecting pixels are arranged in a row so that signals from the pixels are serially output upon a scanning control signal being offered.

Preferably, the one dimension image sensor is optically arranged so that the sensor scans a wider side of the flow of the sample solution in the direction across the flow of the sample solution, when the flow is rectangular or ellipsoidal.

The optical deflection means according to the present invention may be of any kind as long as it can receive control signal to deflect the optical path when the optical deflection means is disposed in a certain optical path. Specifically an angle variable prism, an acousto-optic deflector or a galvano-mirror can be used.

The control means according to the present invention acts to control the deflection angle of the optical deflection means so that the one dimension sensor optically tracks and scan the particle that travels in the sample solution flow. In other words, control of the deflection angle allows an image detection area on the particle to shift in the direction in which the particle moves. Consequently, the relative speed of the particle as seen from the one dimension image sensor is substantially lowered with the result that the analysis precision of the particle is improved.

When the deflection angle of the optical deflection means is controlled so that a particle traveling at a speed of V1 in the sample solution flow is optically tracked by the one dimension sensor at a speed V2 (>0) slower than V1, a relative speed of the particle is decreased to a level of V1−V2 as seen from the one dimension image sensor. As a result, the number of time of scanning one particle by the image sensor increases.

For example, when V1 is set to 500 mm/sec and V2 to 450 mm/sec, the equation of V1−V2=50 mm/sec is established. When the scanning frequency assumes 50 KHz, one particle (for example, a red blood cell) having a diameter of 8 microns can be scanned 8 times.

The control means initiates the control of the optical deflection means based on the output signal of the one dimension image sensor.

The signal processing means may further provide means for outputting a scanning signal. The one dimension image sensor may output the image signal of the particle in synchronization with the scanning signal.

The present invention provides a particle image analyzing apparatus comprising: a flow cell for enclosing a solution containing a particle to be analyzed in a sheathed flow to form the solution into a sample solution flow; a first irradiation optical system for emitting first light to irradiate the sample solution flow; a one dimension image sensor for receiving the first light transmitted through the particle to scan the particle and output an image signal; optical deflection means for deflecting the transmitted first light introduced to the image sensor; control means for controlling a deflection angle of the optical deflection means such that the image sensor optically tracks the particle; a second irradiation optical system for emitting second light to irradiate the particle irradiated with the first light; light detecting means for detecting scattered light and/or fluorescence from the particle irradiated with the second light and for outputting a detected signal; and signal processing means for analyzing the particle based on the output signals from the image sensor and the light detecting means. Preferably, the first light is different from the second light in wavelength.

The light detecting means comprises means for detecting the scattered light from the particles and the control means initiates the control of the deflection angle of the optical deflection means based on the output signal from the means for detecting the scattered light.

The light detecting means comprises means for detecting the fluorescence from the particles and the control means may initiate the control of the deflection angle of the optical deflection means based on the output from the means for detecting the fluorescence.

The present invention will be detailed hereinbelow in conjunction with the accompanying drawings. However, the quality of the material, the configuration, the relative arrangement of constituent devices described in the embodiments are not intended to limit the scope of the present invention unless otherwise indicated. They are merely given for illustrating the invention.

Embodiment 1

FIG. 1(a) is a view (side view) illustrating the basic construction of a particle image analyzing apparatus of the present invention. Reference Numeral 18 designates a flow cell for forming a flat sample solution flow 19. The flow cell 19 is formed of a transparent material such as glass, plastic or similar material. The sample solution flow (sample flow) 19 containing a particle to be analyzed is introduced into the flat flow cell 18. Thus a sheathed solution is supplied so that the sheathed solution encloses the circumference of the sample flow thereby forming a flat sheathed flow.

The sample solution flow 19 flows in the Z direction (vertical direction on the paper). The sample solution flow is a flat flow which has a width approximately the same as the particle diameter in the Y direction (right-to-left direction on the paper) and a wide width several times larger than the particle diameter in the X direction (perpendicular to the paper). Reference Numeral 24 denotes a one dimension image sensor, that is, a CCD line sensor whose pixels are arrayed in a single line extending in the X direction.

Figure 2:
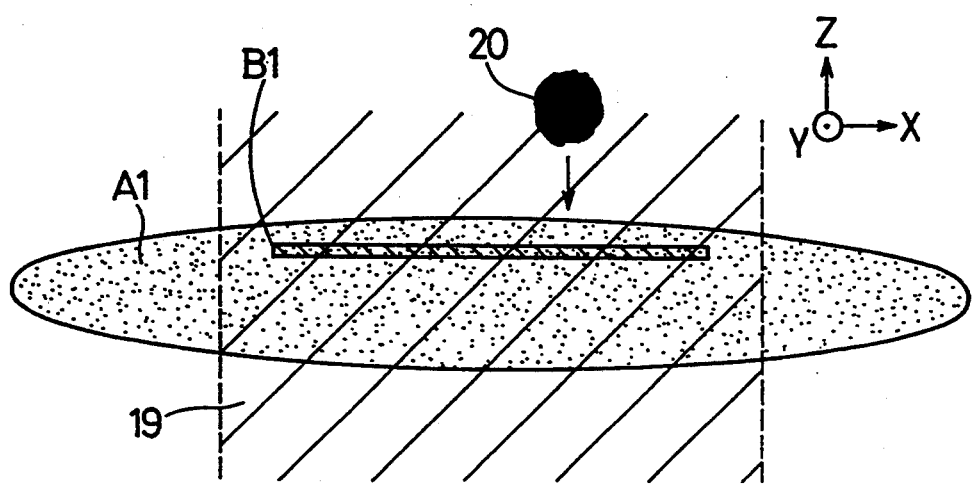
FIG. 2 is an enlarged view of a flow portion of a sample solution when a flow cell is observed from the side of the optical axis in FIG. 1(a), the view illustrating a detection area B1 of a line sensor and an irradiation area A1 of the irradiation light.

FIG. 2 is an enlarged view of a sample solution flow portion when the flow cell is observed from the image sensor 24. Reference Numeral 20 designates a particle to be analyzed (such as hemocytes or cells). Symbol B1 designates a linear image detection area of the line sensor 24 formed on the sample solution flow 19. Detecting pixels of the line sensor 24 are arranged in a row in the X direction.

Referring to FIG. 1(a), a collimator lens 12 converts white light emitted from a light source 10 into collimated light. Then a cylindrical lens 16 further converts the collimated light into oblong-like light having a wider width in the X direction than the width of the sample solution flow 19 and having a width several times larger than the particle diameter in the Z direction to be directed to an oblong-like area A1 including the detection area B1, as shown in FIG. 2. In other words, the area A1 constitutes a irradiation area of light emitted from the light source 10. The light source 10, the collimator lens 12, and the cylindrical lens 18 constitute an irradiation optical system.

When the particle 20 travels in the direction shown by an arrow in FIG. 2 and reaches the detection area B1, the transmitted light that passes through the particle 20 is directed onto the receiving surface of the line sensor 24 via an object lens 22 and a projection lens 23 shown in FIG. 1(a) to form an image thereon. The line sensor 24 scans the particle 20 by traversing it to output an image signal Si synchronized with each scanning signal i. The image signal Si is input to a signal processing system 26 where several kinds of property parameters concerning each particle are determined in real time based on the image signal Si. Incidentally, the scanning signal i is a synchronization signal generated in the signal processing system 26.

Figure 1B:
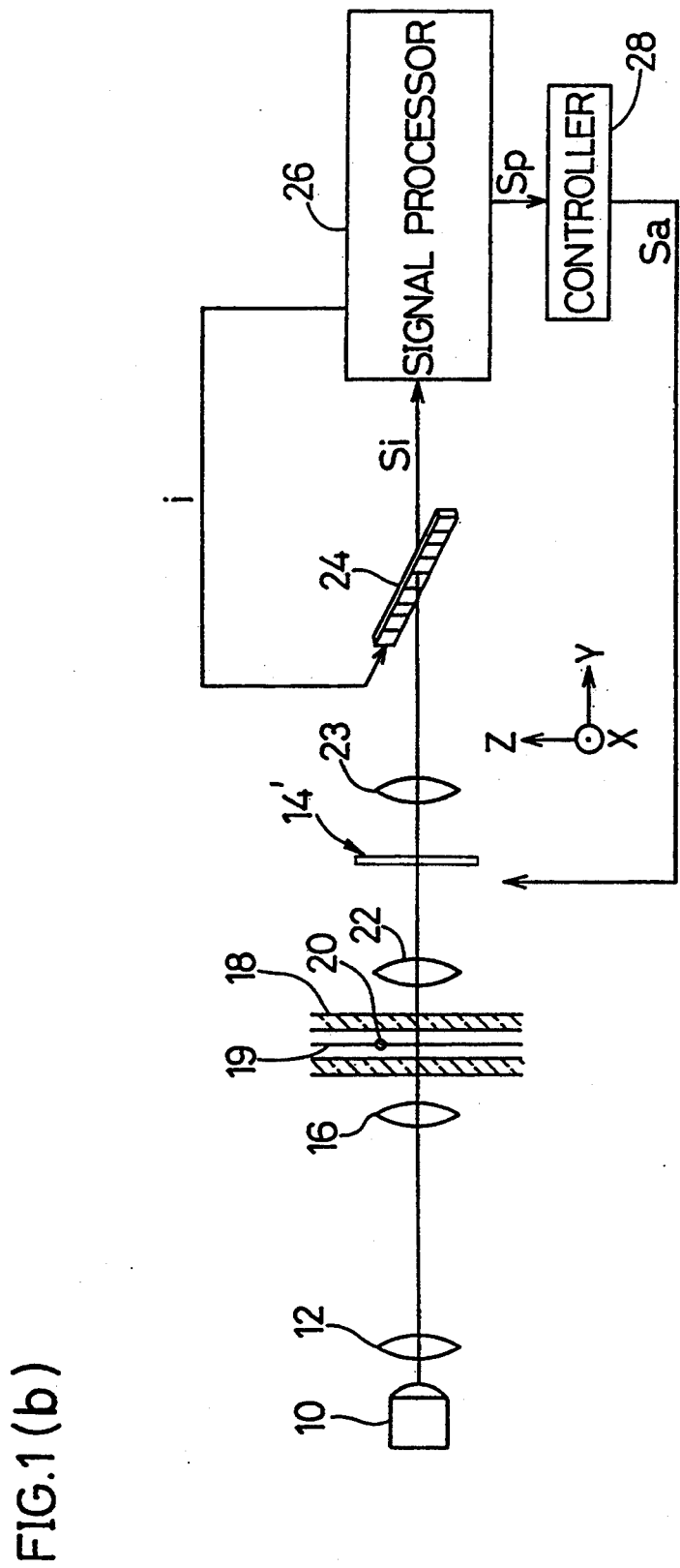
FIG. 1(b) is a particle image analyzing apparatus including an acousto-optic deflector.
Figure 1C:
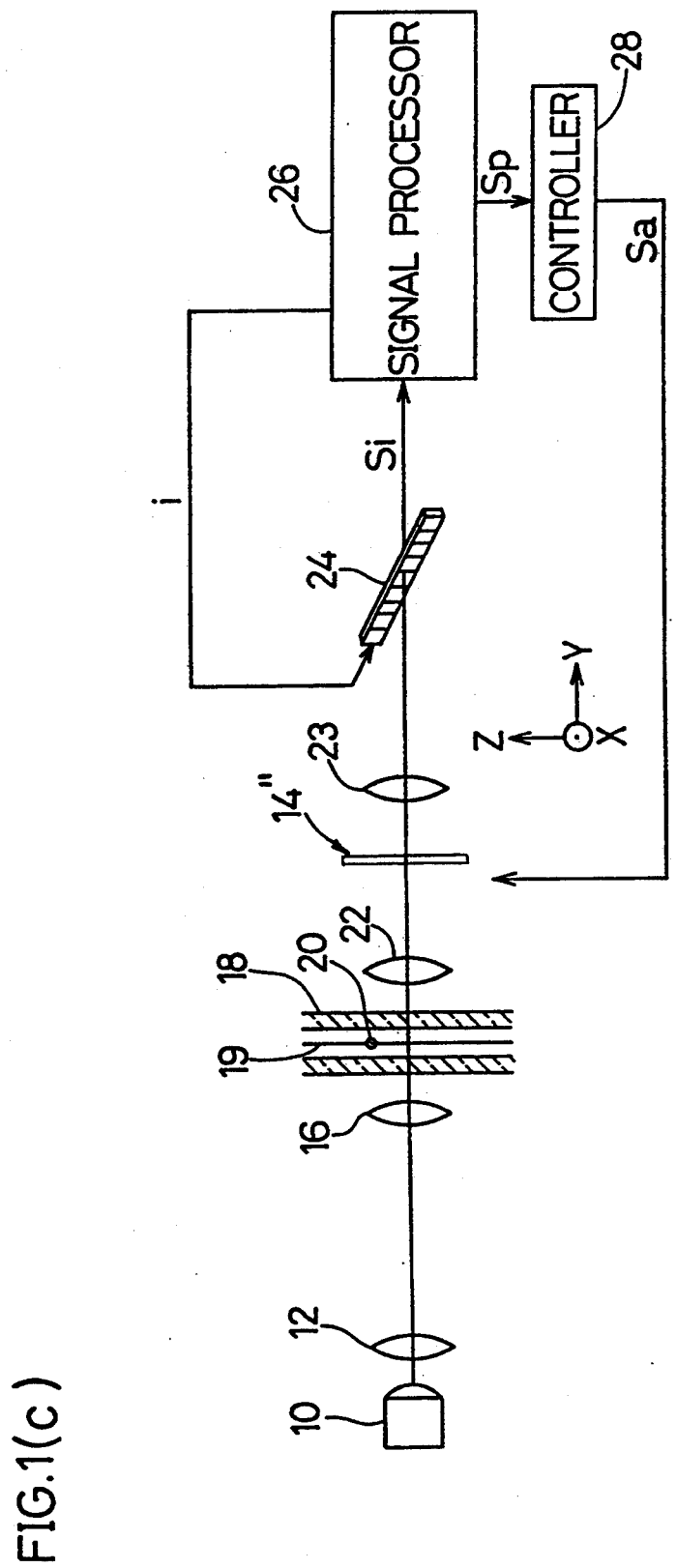
FIG. 1(c) is a particle image analyzing apparatus including a galvano-mirror, according to the present invention.

In the apparatus according to the present invention, an angle variable prism 14 is provided as an optical deflection means in the optical path from the flow cell 18 to the line sensor 24 (between the object lens 22 and the projection lens 23 in FIG. 1(a)). The optical deflection means changes the direction of an optical axis. In concrete terms, the optical deflection means includes the angle variable prism comprising an optical fluid having a high refraction index and two transparent plates sandwiching the fluid therebetween wherein the direction of light passing through the fluid can be changed by varying the tilt of the two transparent plates, an acousto-optic deflector (AOD) 14' as shown in FIG. 1(b), in which the light direction can be changed by transmitting an ultrasonic wave into an optical medium and changing the frequency of the ultrasonic wave, and a galvano-mirror 14' as shown in FIG. 1(c), in which the light direction can be changed by changing the angle of a mirror. A typical angle variable prism, acousto-optic deflector, and galvano-mirror are available from Canon Kabushiki Kaisha (Japan), HOYA CORPORATION (Japan) and General Scanning Inc (U.S.A.), respectively.

Preferably, the incident light that enters into the angle variable prism 14 is collimated light. As the object lens 22, a lens of infinitely distant focusing type can be used.

Figure 3:
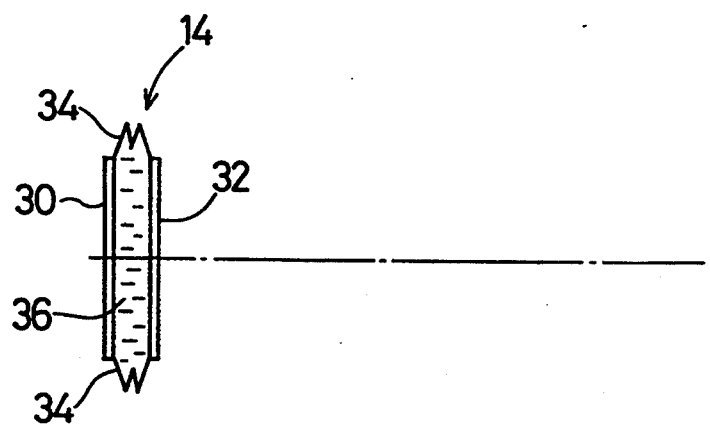
FIG. 3 is a view illustrating the initial state of an angle variable prism of FIG. 1(a).
Figure 4:
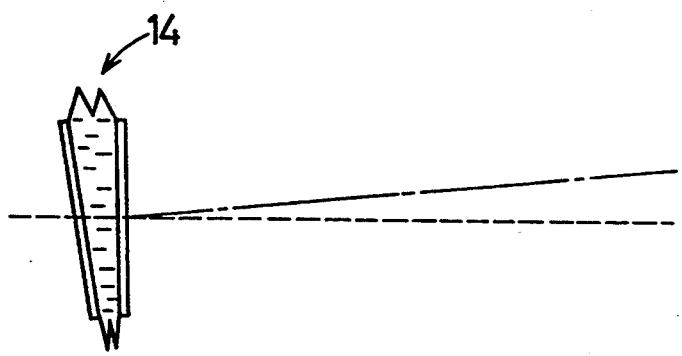
FIG. 4 is a view illustrating the deflected state of the angle variable prism of FIG. 1(a).

FIGS. 3 and 4 are schematic views illustrating the construction of the angle variable prism 14. FIG. 3 shows an initial state whereas FIG. 4 shows a deflected state. The angle variable prism 14 comprises two transparent plates 30, 32 (for example, glass plate or a plastic plate), a bellows 34 connecting the peripheries of the two transparent plates 30, 32, and a transparent liquid material 36 (for example, silicone liquid) having a high reflection index sealed between the two transparent plates. By changing the angle of two plates 30, 32 by an electric driving means (not shown in the drawings) such as a voice coil or the like, light can be deflected from a broken line to a chain line as shown in FIG. 4.

When the angle variable prism 14 is placed in the state shown in FIG. 3, the detection area B1 is set to the up-stream portion of the sample solution flow 19 in the irradiation area A1 as shown in FIG. 2. The angle variable prism 14 moves the detection area B1. When the particle 20 that has been flowing contacts the detection area B1, the image signal Si obtained by the line sensor 24 scanning the top of the particle 20 is sent to the signal processing system 26. Based on the image signal Si, the signal processing system 26 initiates the generation of a particle detection timing signal Sp and sends the signal Sp to a controller 28 (shown in FIG. 1). The controller 28 generates an angle control signal Sa based on the particle detection timing signal Sp. This control signal Sa controls the deflection angle of the angle variable prism 14 such that the linear image detection area B1 is moved in the same direction as the flow of the particle 20.

Figure 5:
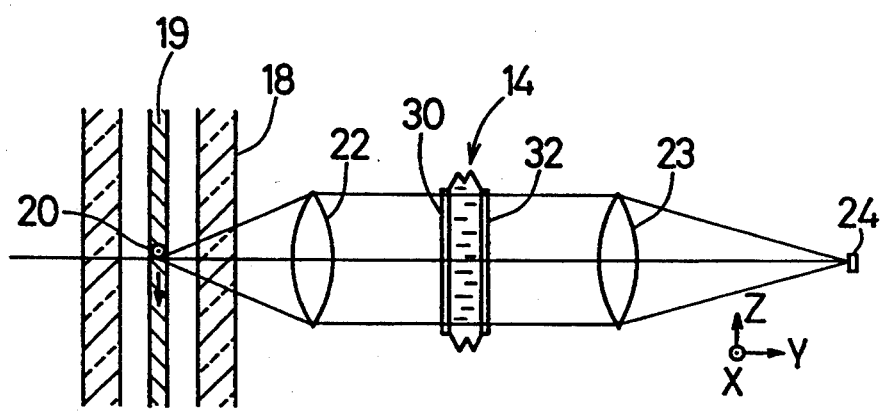
FIG. 5 is an enlarged view illustrating the initial state of the image forming optical system portion of FIG. 1(a).
Figure 6:
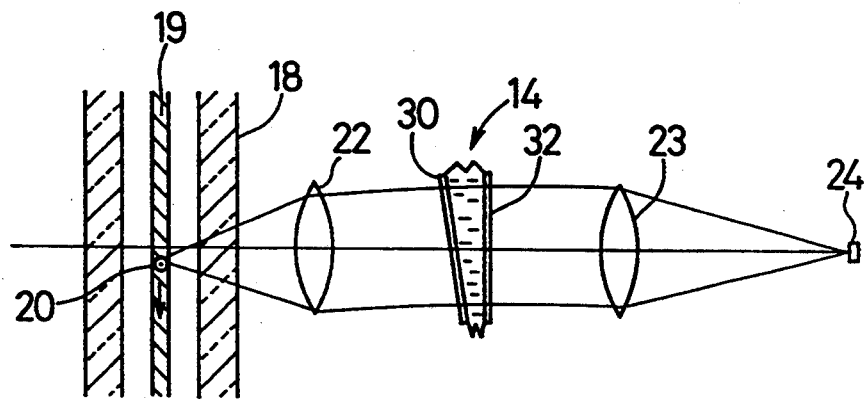
FIG. 6 is a view illustrating the deflected state of the image forming optical system portion of FIG. 1.
Figure 7:
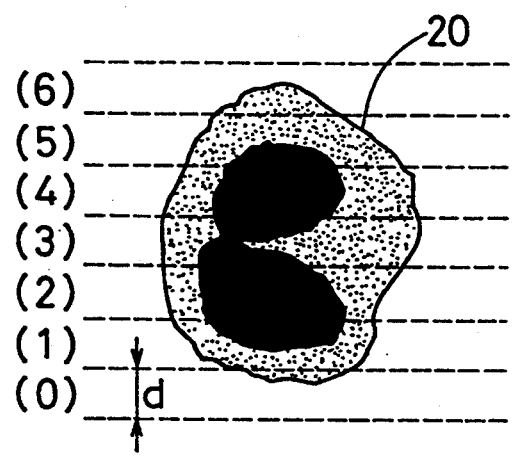
FIG. 7 is a view illustrating one example of scanning a cell (particle).
Figure 8:
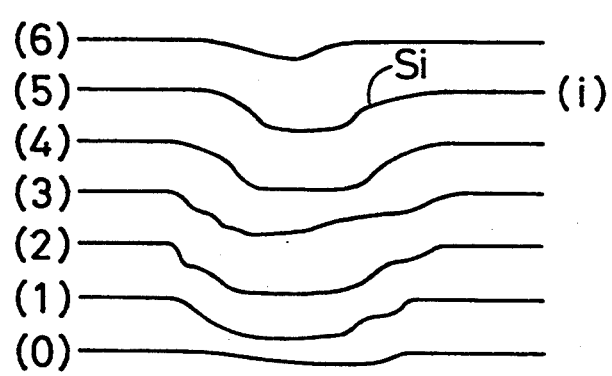
FIG. 8 is a waveform view illustrating one example of a video signal output from the line sensor in synchronization with the scanning signal i.

FIGS. 5 and 6 are views illustrating an image forming optical system portion. FIG. 5 illustrates a state in which the particle 20 has reached the upper end of the detection area B1, namely the initial state thereof. The two glass plates in the angle variable prism 14 are parallel to each other. Along with the movement of the particle 20, the two glass plates 30, 32 begin to form an angle and the detection area B1 moves in the same direction (downward direction in FIGS. 5 and 6) as the particle at a speed V2, slower than the moving speed V1 of the particle. This makes it possible to diminish the speed (V1−V2) of the particle relative to the detection area B1 rather than the actual moving speed V1. In other words, by setting V1 and V2 to the relationship of V1>V2>0, the relative moving speed of the particle can be reduced. In the meantime, as shown in FIG. 7, one particle can be scanned a plurality of times by changing the scanning portion thereof. Incidentally, numerals in the round brackets ( ) in FIG. 7 designate the number of the scanning cycles. Symbol d designates a distance in which one particle moves for one scanning cycle. FIG. 8 designates the image signal Si the line sensor 24 successively outputs synchronized with the scanning signal i. Incidentally, the signal processing system 26 continuously outputs the particle detection timing signal Sp to the controller 28 while the system 26 receives the image signals of Nos. 0 through 6. That is, the prism 14 begins to increase its deflection angle with the image signal of No. 0 and finishes with the image signal of No. 6.

In this manner the apparatus of the present invention scans one particle a plurality of times which travels at a higher speed than the conventional one. In addition, when the particle travel speed is approximately the same as the conventional counterpart, this apparatus can scan one particle more times than the conventional apparatus (this means that a more precise analysis for the particle image can be performed).

Figure 11:
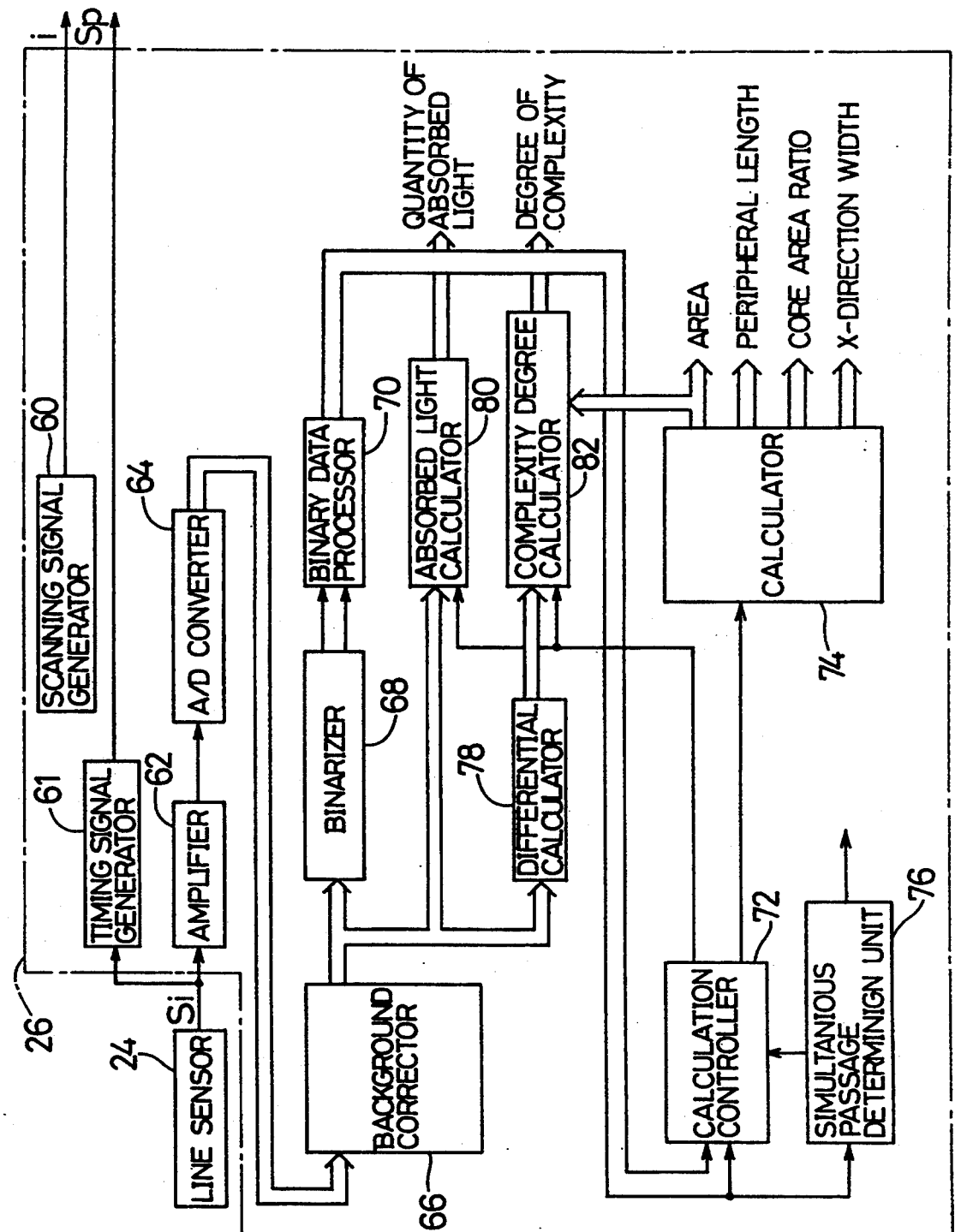
FIG. 11 is a black view illustrating a signal processing apparatus in the first embodiment.

FIG. 11 shows one example of the signal processing system 26 for processing a detection signal Si that can be obtained from the line sensor 24. Reference Numerals 60, 61 designate respectively a generator of the scanning signal i and a generator of the particle detection timing signal Sp.

The signal Si given by the line sensor 24 is amplified by an amplifier 62, and A/D converted by an A/D converter 64. The data generated is corrected by a background corrector 66. In the background corrector 66, one-line data is held in a memory in advance, which is generated by a transmitted light when the particle is not passing through the detecting area B1 (shown in FIG. 2). Then processing is performed in real time for determining the difference between the above data and the A/D conversion data given in the measurement. The object of this processing is to correct irradiation non-uniformity and variability in sensitivity of each detecting pixel of the line sensor 24.

A binarizer 68 converts the corrected data into binary-coded data by comparing the corrected data with an appropriate first reference level to pick-up the scope of signals corresponding to the image of transmitted light screened by the particle 20. Furthermore, the binarizer 68 converts the corrected data into binary-coded data by comparing the corrected data with another second reference level higher than the first reference level to pick-up only the vert dark core portion of the particle 20.

The binary-coded data is processed to remove a small dust and classify the scope of the binary-coded data corresponding to each particle. In other words, a binary data processor 70 performs preprocessing for area division. The area division here means determining the scope of binary-coded data (timing) corresponding to one particle. This processing is required for generating a timing control signal for calculating morphological parameters and absorbed light of each particle in real time.

A control signal output from the binary data processor 70 and a calculation controller 72 controls a calculator 74 for determining a quantity of absorbed light, a degree of complexity and morphological parameters, for example area, peripheral length. Thus parameters relative to each particle can be determined in real time.

In addition, based on data processed by binary data processor 70, a simultaneous passage determining unit 76 judges whether or not binary-coded data is of particles simultaneously passing through detecting area B1. The parameters of the particle are ignored by the judgment of the unit 78. Reference Numeral 78 designates a differential calculator, 80 an absorbed light calculator, and 82 a complexity degree calculator. The calculators 80, 82 are controlled by the controller 72. The complexity degree here means a value obtained by dividing by an area an addition of differences between adjacent data of A/D converted detected signals within the scope corresponding to one particle. It is also possible to use as the complexity a value obtained by adding together within the scope corresponding to one particle, squared values of differences between two adjacent data.

Embodiment 2

Figure 9:
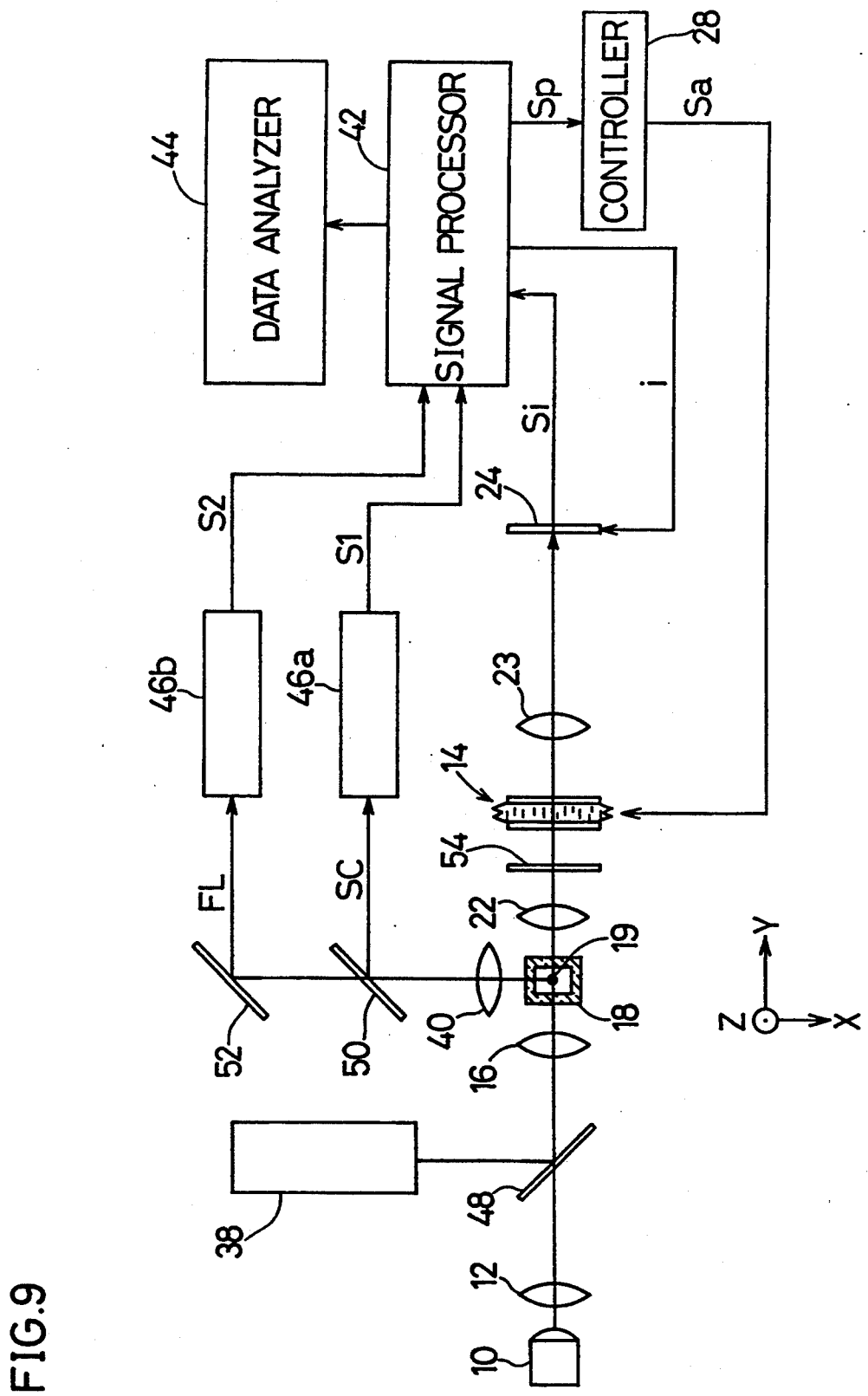
FIG. 9 is a plan view illustrating a second embodiment of the particle image analyzing apparatus of the present invention.

FIG. 9 is a plan view of an apparatus formed by adding to the apparatus of FIG. 1(a) an optical system for detecting scattered light (side scattered light) reflected or refracted by a particle and fluorescence (side fluorescence) emitted by a particle which is treated with a fluorescent dye. Reference Numeral 38 designates a second light source, for example an argon laser emitting a laser beam having a wavelength of 488 nm. In this particular embodiment, the light source 10 emits light having a wavelength different from that of the second light source 38 in the Y direction. The light source 10 is, for example, a laser diode emitting a near infrared light. A laminar sample solution flow flows in the perpendicular direction on the paper (Z direction). The second light source 38 is arranged so that the light emitted by the second light source 38 is in a direction crossing at right angle with the light emitted by the light source 10. The light emitted by the second light source 38 is reflected by a dichroic mirror 48 and elongated by a cylindrical lens 16 in a direction to irradiate a wider side of the sample flow 19. Thus the light emitted by the light source 10 and the light emitted by the light source 38 are directed to a region on the sample solution flow 19 or two adjacent regions on the sample solution flow 19.

When the sample solution contains a particle treated with fluorescent dyes, the particle is excited by the irradiation light of the second light source 38 thereby emitting fluorescence having a wavelength longer than the irradiation light as the side fluorescence. The side fluorescence emitted from the particle, after being collected by a collecting lens 40, passes through a dichroic mirror 50 that allows light having the wavelength of the fluorescence to pass therethrough. The light passing through the dichroic mirror 50 is then reflected by a dichroic mirror 52 and received by a light detector 46b.

The side scattered light caused by the irradiation light from the second light source 38 is reflected by the dichroic mirror 50 and received by the light detector 46a. Incidentally, both the side fluorescence and the side scattered light are so weak that a photomultiplier is used as the light detectors 46a and 46b.

The light emitted by the light source 10 and collimated by the collimator lens 12, after passing through the dichroic mirror 48, is directed to the oblong-like area A1 on the sample solution flow 19 through the cylindrical lens 16 as shown in FIG. 2 in the same manner as FIG. 1(a). The light passing through the particle enters the angle variable prism 14 via the object lens 22 and a filter 54. The filter 54 serves as means for screening the light emitted from the second light source 38 and transmitting only the light emitted from the light source 10.

The light passing through the particle caused by the irradiation light from the light source 10 is deflected by the angle variable prism 14 further passes through the projection lens 23 and forms a particle image on the light receiving surface of the line sensor 24.

In this particular embodiment, a signal processing system 42 outputs the scanning signal i to the line sensor 24 and receives a detection signal S1 from the light detector 46a (or a detection signal S2 from the light detector 46b) to generate the particle detection timing signal Sp. On the other hand, the controller 28 receives the timing signal Sp to output the angle control signal Sa.

Figure 10:
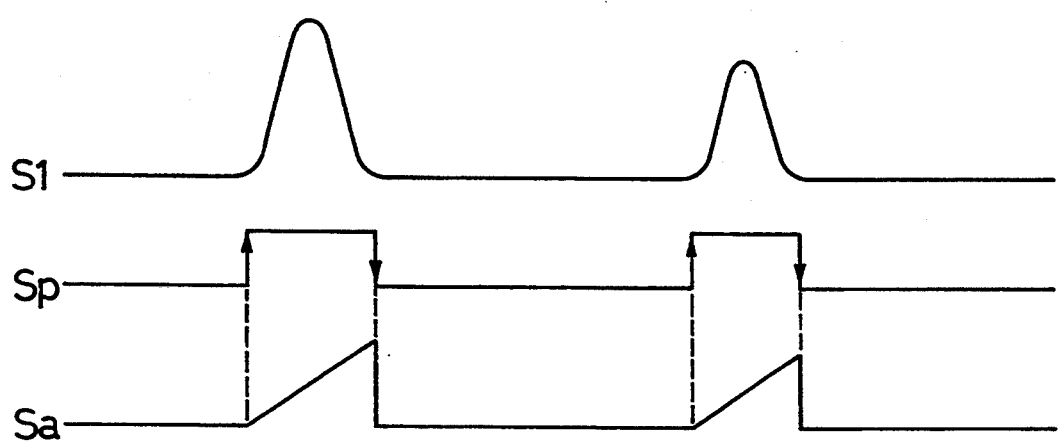
FIG. 10 is a timing chart of a signal S1 of a light detector, a particle detection timing signal Sp and an angle control signal Sa in the second embodiment.

FIG. 10 is a timing chart for signals S1, Sp, and Sa. The signal Sp is a binary-coded signal converted from the signal S1. The angle control signal Sa begins to rise when the signal Sp rises. The signal Sa gradually increases the deflection angle of the angle variable prism 14 corresponding to the travel of the particle. The signal Sa returns to the initial state when the signal Sp falls.

Accordingly, when the detection signal S1 is converted into the signal Sp, particles emitting side scattered light can be scanned and detected by the line sensor 24. On the other hand, when the detection signal S2 is converted into the signal Sp, only particles emitting fluorescence can be scanned and detected by the line sensor 24.

Based on the signals S1, S2 and Si detected by the light detectors 46a, 46b as well as the line sensor 24, characteristic parameters for each particle are determined in real time. The characteristic parameter here means an intensity of the fluorescence, an intensity of the scattered light, morphological data such as an area, a circular degree and the like, a light absorbency and a complexity degree. A method for determining these characteristic parameters are given in the specifications of U.S. patent applications Ser. Nos. 07/937,340 and 08/070,667 filed by the applicants of the present invention.

In other words, the light detector 46b detects an intensity of the fluorescence whereas the light detector 46a detects an intensity of the side scattered light.

In addition, by entering into the signal processing system 42, the image signal Si from the line sensor 24, morphological data and light absorbency data of the particle can be obtained.

Each of the characteristic parameters obtained in the signal processing system is transmitted to a data analyzer 44 which creates a two dimension scattergram and one dimension histogram thereby analyzing the particle such as classification or the like with great accuracy.

The present invention constituted as mentioned above has the following advantages.

The optical deflection means is added to the optical system for obtaining an optical image of the particle with the transmitted light to move the detection area on the particle along with the travel of the particle. Consequently, the relative travel speed of the particle relative to the detection area can be slowed down. Even when the actual travel speed of the particle is increased, one particle can be scanned plural times. In other words, the number of particles analyzed per unit time can be increased.

Alternatively when the travel speed of the particle is not increased, the number of scanning operations can be increased with respect to one particle. That is, the image resolution in the flow direction of particles can be improved and the characteristic parameter like morphological data can be determined with good accuracy.

What is claimed is:

1. A particle image analyzing apparatus comprising:
   a flow cell for enclosing a solution containing particles to be analyzed in a sheathed flow to form the solution into a sample solution flow;
   an irradiation optical system for emitting light to irradiate an irradiation area on the sample solution flow;
   a one dimension image sensor for defining an elongated detection area across the sample solution flow within the irradiation area and receiving light transmitted through a part of the particle in the elongated detection area to scan the particle across the sample solution flow and output an image signal, the detection area having a width narrower than a diameter of the particle;
   optical deflection means disposed between said flow cell and said one dimension image sensor for variably deflecting the transmitted light introduced to the image sensor;
   control means for controlling a deflection angle of said optical deflection means such that said one dimension image sensor optically tracks the particle at a speed different from a travelling speed of said particle; and
   signal processing means for processing an output image signal of said one dimension image sensor to analyze the particle.

2. The apparatus according to claim 1 wherein said control means controls the deflection angle of said optical deflection means so that the one dimension image sensor optically tracks at a speed of V2, the particle traveling at a speed of V1, and the speeds V1 and V2 are related such that $V1 > V2 > 0$, so that the image sensor scans the same particle a plurality of times.

3. The apparatus according to claim 1 wherein said control means initiates control of the deflection angle of said optical deflection means based on the output image signal of the one dimension image sensor.

4. The apparatus according to claim 1 wherein said signal processing means includes means for outputting a scanning signal in a cycle and said one dimension image sensor outputs the image signal in synchronization with the scanning signal.

5. The apparatus according to claim 1 wherein the sample solution flow is a flat flow and said irradiation optical system irradiates a wider side relative to the sample solution flow.

6. The apparatus according to claim 1 wherein said optical deflection means comprises an angle variable prism that deflects light by varying the thickness of an optical medium disposed between two transparent plates, the optical medium having a high refraction index.

7. The apparatus according to claim 1 wherein said optical deflection means comprises an acousto-optic deflector.

8. The apparatus according to claim 1 wherein said optical deflection means comprises a galvano-mirror.

9. A particle image analyzing apparatus comprising:
   a flow cell enclosing a solution containing a particle to be analyzed in a sheathed flow to form the solution into a sample solution flow;
   a first irradiation optical system for emitting first light to irradiate an irradiation area on the sample solution flow;
   a one dimension image sensor for defining an elongated detection area within the irradiation area and receiving the first light transmitted through a part of the particle in the detection area to scan the particle across the sample solution flow and output an image signal, a width of the detection area having a width narrower than a diameter of the particle;
   optical deflection means, disposed between said flow cell and said one dimension image sensor, for variably deflecting the transmitted first light introduced to said one dimension image sensor;
   control means for controlling a deflection angle of said optical deflection means such that said one dimension image sensor optically tracks the particle at a speed different from a travelling speed of said particle;

a second irradiation optical system for emitting a second light to irradiate the particle irradiated with the first light;

light detecting means for detecting at least one of scattered light and fluorescence from the particle caused by the second light and for outputting a detected signal; and signal processing means for analyzing the particle based on the image signal from said one dimension image sensor and the detected signal from said light detecting means.

10. The apparatus according to claim 9 wherein the first light is different from the second light in wavelength.

11. The apparatus according to claim 9 wherein said light detecting means comprises scattered light detecting means for detecting the scattered light from the particle, and said control means initiates control of the deflection angle of said optical deflection means based on an output signal from said scattered light detecting means.

12. An apparatus of claim 9 wherein said light detecting means comprises fluorescence detecting means for detecting the fluorescence from the particle, and said control means initiates control of the deflection angle of optical deflection means based on an output signal from said fluorescence detecting means.

13. The apparatus according to claim 9 wherein said optical deflection means comprises an angle variable prism that deflects light by varying the thickness of an optical medium disposed between two transparent plates, the optical medium having a high refraction index.

14. A particle image analyzing method comprising the steps of:

enclosing a solution containing particles to be analyzed in a sheathed flow to form said solution into a sample solution flow;

emitting light to irradiate said sample solution flow;

scanning said particle by a one dimension image sensor which receives said light transmitted through said particle;

controlling a deflection angle of said light after transmission through said particle such that said one dimension image sensor optically tracks said particle at a speed different from a travelling speed of said particle; and processing an output image signal of said one dimension image sensor to analyze said particle.

15. The particle image analyzing method of claim 14, wherein said controlling step comprises the substep of;

controlling said deflection angle so that said one dimension image sensor optically tracks at a speed of V2, said particle traveling at a speed of V1, and said speed V1 and speed V2 are related such that $V1 > V2 > 0$, so that said sensor scans the sample particle a plurality of times.

16. The particle image analyzing method of claim 14, wherein said controlling step comprises the substep of;

initiating control of said deflection angle based on said output image signal of said one dimension image sensor.

17. The particle image analyzing method of claim 14, wherein said controlling step comprises the substep of;

outputting a scanning signal in a cycle; and outputting said output image signal in synchronization with said scanning signal.

18. The particle image analyzing method of claim 14, wherein said scanning step comprises the substep of;

scanning said particle in a direction across said sample solution flow.

19. A particle image analyzing method comprising the steps of:

enclosing a solution containing particles to be analyzed in a sheathed flow to form said solution into a sample solution flow;

emitting first light to irradiate said sample solution flow;

scanning said particle by a one dimension image sensor which receives said first light transmitted through said particle;

controlling a deflection angle of said first light after transmission through said particle such that said one dimension image sensor optically tracks said particle at a speed different from a travelling speed of said particle;

emitting second light to irradiate said particle;

detecting at least one of scattered light and fluorescence from said particle caused by said second light; and analyzing said particle based on a signals obtained by said scanning step and said detecting step.

20. The particle image analyzing method of claim 19, wherein a wavelength of said first light is different from a wavelength of said second light.

21. The particle image analyzing method of claim 19, wherein said controlling step further comprises the substep of:

initiating control of said deflection angle based on an output signal obtained by a detection of said scattered light in said controlling step.

22. The particle image analyzing method of claim 19, wherein said controlling step further comprises the substep of:

initiating control of said deflection angle based on an output signal obtained by a detection of said fluorescence in said controlling step.

* * * * *